United States Patent [19]
Hardy et al.

[11] Patent Number: 6,011,828
[45] Date of Patent: *Jan. 4, 2000

[54] LASER MEASURING APPARATUS AND METHOD FOR RADIOSURGERY/ STEREOTACTIC RADIOTHERAPY ALIGNMENT

[75] Inventors: Tyrone L. Hardy, Del Mar; Laura R. D. Brynildson, San Diego, both of Calif.

[73] Assignee: Medical Instrumentation and Diagnostics Corporation (MIDCO), N.Mex.

[*] Notice: This patent is subject to a terminal disclaimer.

[21] Appl. No.: 09/185,372

[22] Filed: Nov. 3, 1998

Related U.S. Application Data

[63] Continuation of application No. 08/466,240, Jun. 6, 1995, Pat. No. 5,553,112.

[51] Int. Cl.$^7$ .................................................. A61N 5/10
[52] U.S. Cl. ............................................. 378/65; 378/206
[58] Field of Search ....................................... 378/65, 206

[56] References Cited

U.S. PATENT DOCUMENTS

| | | |
|---|---|---|
| 3,783,251 | 1/1974 | Pavkovich . |
| 4,123,143 | 10/1978 | Yachin et al. . |
| 4,223,227 | 9/1980 | Horwitz . |
| 5,027,818 | 7/1991 | Bova . |
| 5,099,846 | 3/1992 | Hardy . |
| 5,107,839 | 4/1992 | Houdek et al. . |
| 5,142,559 | 8/1992 | Wielopolshi . |
| 5,398,684 | 3/1995 | Hardy . |
| 5,553,112 | 9/1996 | Hardy et al. ............................. 378/65 |

OTHER PUBLICATIONS

Drzymala, R.E., "Quality Assurance for Linac–Based Stereotactic Radiosurgery," allinckrodt Institute of Radiology, Washington University Medical School (St. Louis MO pp. 121–129.

Friedman, W.A., et al., "The University of Florida Radiosurgery System," *Surg. Neurol*, vol. 32, pp. 334–342 (1989).

Keyence Corp., "Laser Displacement Sensors," Keyence LB–1000 Series Instruction Manual (1994).

Lutz, W., et al., "A System for Stereotactic Radiosurgery with a Linear Accelerator," *L.J. Radiation Oncology/Biology/Phsics*, vol. 14, No. 3, pp. 373–381 (Feb. 1988).

Podgorsak, E.B., "Radiosurgery with High Energy Photon Beams: A comparison Among Techniques," *L.J. Radiation Oncology/Biology/Physics*, vol. 16, No. 3, pp. 857–865 (Mar. 1989).

Podgorsak, E.R., "Physics for Radiosurgery with Linear Accelerators," *Stereotactic Radiosurgery*, vol. 3, No. 1, pp. 9–33 (Jan. 1992).

Serago, C.F., et al., "Stereotactic Target Point Verification of an X Ray and CT Localizer," *L.J. Radiation Oncology/Biology/Physics*, vol. 20, No. 3, pp. 517–523 (Mar. 1991).

Winston, K.R., et al., "Linear Accelerator as a Neurosurgical Tool for Stereotactic Radiosurgery," *Neurosurgery*, vol. 22, No. 3, pp. 545–462 (1988).

*Primary Examiner*—Craig E. Church
*Attorney, Agent, or Firm*—Deborah A. Peacock; Jeffrey D. Myers; Rod D. Baker

[57] ABSTRACT

An apparatus and method for aligning a radiosurgery/ stereotactic radiotherapy system. The system includes a linear accelerator, including a gantry and a collimator, a couch, and a stereotactic reference system mounted on the couch. The apparatus includes a laser measuring device mounted on the gantry, the laser measuring device having a laser generator element for generating a laser light beam and a laser displacement sensor. The apparatus also includes a reference fixture, attached to the stereotactic reference system, having at least one reflective surface for reflecting the laser light beam to the laser displacement sensor, upon which the laser displacement sensor measures the distance between the reflective surface and the laser measuring device.

22 Claims, 8 Drawing Sheets

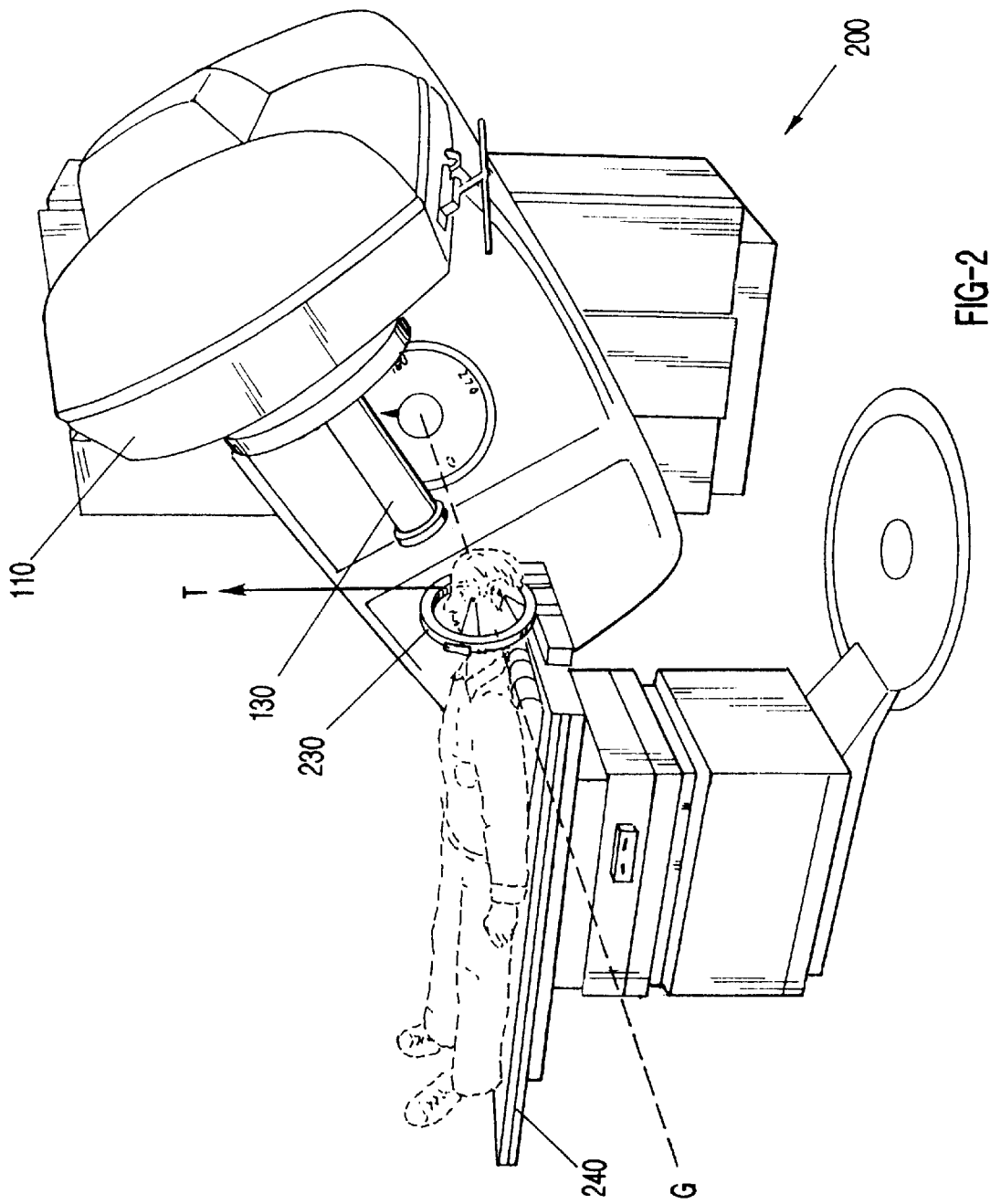

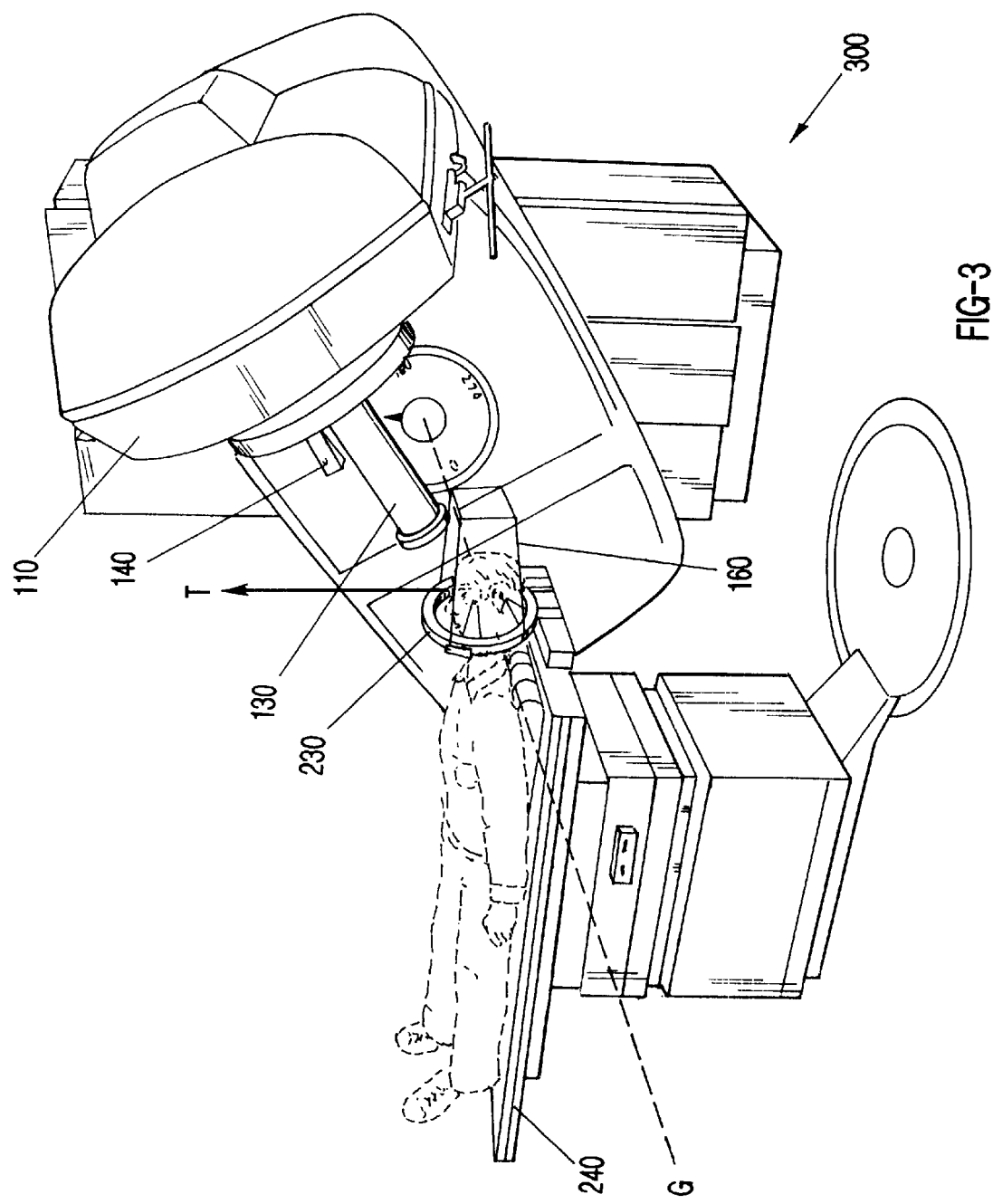

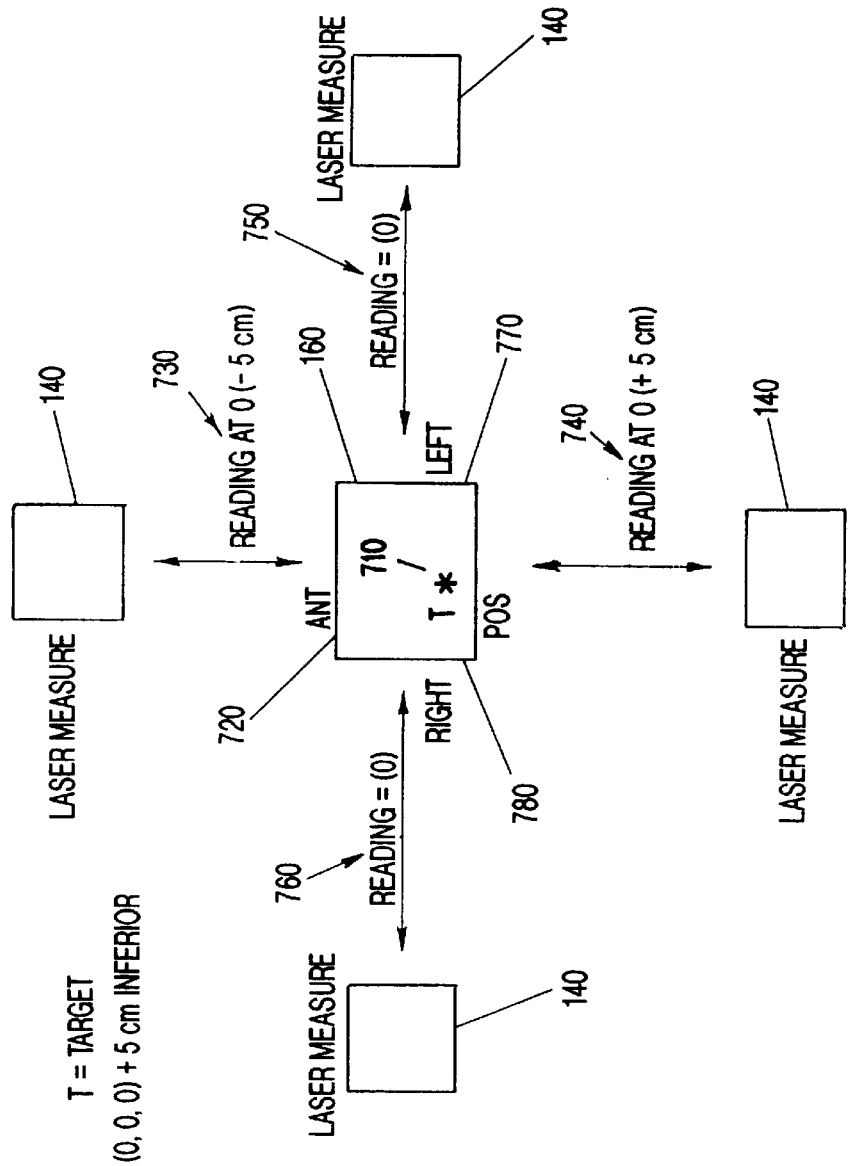

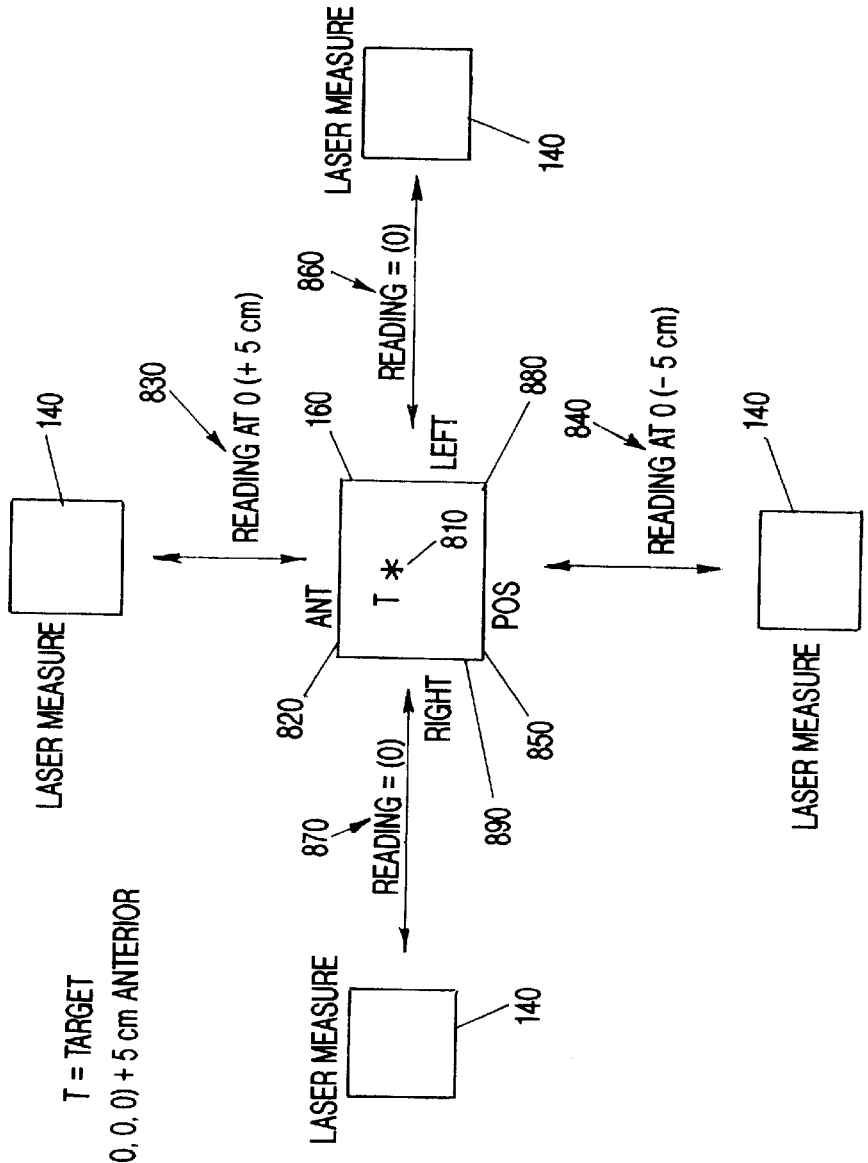

LASER MEASURING APPARATUS AND METHOD FOR RADIOSURGERY/ STEREOTACTIC RADIOTHERAPY ALIGNMENT

This application is a continuation of Ser. No. 08/466,240 filed Jun. 6, 1995, now U.S. Pat. No. 5,553,112.

A portion of the disclosure of this patent document contains material subject to copyright protection. The owner has no objection to the facsimile reproduction by anyone of the patent document or the patent disclosure as it appears in the Patent and Trademark Office patent file or records, but otherwise reserves all copyright rights whatsoever.

BACKGROUND OF THE INVENTION

1. Field of the Invention

The present invention relates to a measuring apparatus and method for radiosurgery/stereotactic radiotherapy alignment. More particularly, the present invention relates to a method and apparatus for precisely measuring the isocenter of a target volume for a linear accelerator ("Linac") based radiosurgery/stereotactic radiotherapy system, thereby also compensating for or correcting alignment errors during treatment planning, such as errors due to misalignment of room laser alignment systems and couch (or table) or gantry sag, shifts, or misalignments.

2. Description of Related Art

Historically, several Linac based techniques have been used for the delivery of high-energy photon beams as a means for radiosurgery/stereotactic radiotherapy. These various methods have been reviewed by E. B. Podgorsak, Physics for Radiosurgery with Linear Accelerators, in Neurosurgery Clinics of North America, Vol. 3, No. 1, January, 1992. As therein noted, the system of multiple co-planar arcs is by far the most prevalent. These techniques have also varied with regard to the method of stereotactic head fixation during treatment, wherein the aim is to accurately align a target volume (isocenter in the patient's head or body part) within the centers of rotation of the couch/gantry coordinate system of the linear accelerator. The most common methods employed include either fixation of the stereotactic head frame to the radiotherapy couch ("couchmount systems") or fixation to a rigid floorstand mounted in the revolving floor plate of the Linac radiotherapy couch ("floorstand systems"). See, e.g., Podgorsak, supra; U.S. Pat. No. 5,027,818.

In the practice of the art, it is generally accepted that accuracy requirements for delivery of a radiation beam to a target volume isocenter should have fractions of a millimeter of accuracy, and some authors of floorstand systems have reported such accuracy in mechanical localization. In addition, floorstand systems have generally relied upon the use of phantom test targets that are x-rayed as part of the simulation set-up with the Linac for localization. This method of calibration makes use of a phantom test target placed at a given stereotactic coordinate, and then placed at the center of rotation of the Linac couch/gantry system. The Linac is then used to take test target x-rays with the couch and gantry in several different positions of rotation for the purpose of accurately aligning the stereotactic reference system. Couchmount systems are generally not as accurate as floorstand systems and have relied upon fixed room laser lights projected on a phantom carriage device for target localization within the Linac couch/gantry coordinate system. See, e.g., U.S. Pat. Nos. 4,123,143 and 4,223,227.

Although head fixation to a floorstand mounted in the Linac floor turret has historically been regarded by many as the most reliable and accurate method, it greatly limits the accessibility to the patient's head. This is particularly noticeable for lesions in the posterior portions of the head that frequently require that the patient be treated in the prone position when using such floorstand-based systems. In addition, floorstand-based systems require that the gantry of the Linac be specially rigged to protect against the possibility of accidental collision of the gantry with the floorstand during the execution of any treatment plan. Couchmount systems, on the other hand, have the advantage of being able to treat a given patient with the potential of a full 360 degrees of gantry rotation and, thereby, allowing the patient to be treated in a natural supine position, while also avoiding the need for gantry collision protection. See, e.g., Podgorsak, supra; U.S. Pat. No. 5,107,839.

The couchmount systems are desirable for the above-noted reasons; yet they have a significant disadvantage in that patient head fixation and stabilization within the coordinate system of the couch/gantry rotations of the Linac are generally not as accurate as floorstand-based systems. This is due to sagging and/or tilting of the couch which can occur in couchmount systems when weight, as weight of a patient's body, is applied to the couch tabletop after initial alignment. Such positional shifts are a source of error in couchmount systems. Some have attempted to solve this problem by cumbersome methods of bracing the couch tabletop, or the use of fixed, intersecting laser beams arranged as intersecting lines and emitted from laser alignment devices attached to the ceilings and walls of the room in which the Linac is housed for the purpose of referencing the origin of the Linac couch/gantry axes of rotation. U.S. Pat. Nos. 4,223,227 and 4,123,143. Such laser lights are commonly employed in the art of radiation therapy, are also known in the art to frequently shift and require recalibration or alignment, and can introduce yet another source of error in target alignment within the couch/gantry coordinate system. Furthermore, such laser beams are usually 2–3 mm wide and can also reduce the accuracy of alignment because of the thickness of the alignment beams and parallax. This aforementioned method relies on the use of lasers for visual alignment and no method, until the Applicants' invention, has been developed for the use of lasers for precise measurement of distances as a means for target volume localization within the couch/gantry coordinate system of a Linac-based radiosurgery/stereotactic radiotherapy system.

Therefore, a need exists for an apparatus and method for precisely measuring the isocenter of a target volume for a Linac based radiosurgery or stereotactic radiotherapy system, particularly in couchmount systems.

SUMMARY OF THE INVENTION

Accordingly, the present invention is directed to a laser measuring apparatus and method for radiosurgery/stereotactic radiotherapy alignment that substantially obviates one or more of the problems due to limitations and disadvantages of the related art.

Additional features and advantages of the invention will be set forth in the description that follows, and in part will be apparent from the description, or may be learned by practice of the invention. The objectives and other advantages of the invention will be realized and attained by the apparatus and method particularly pointed out in the written description and claims of this application, as well as the appended drawings.

To achieve these and other advantages, and in accordance with the purpose of the invention as embodied and broadly described herein, the invention is a method and apparatus for precisely aligning the isocenter(s) of a stereotactic target volume within the centers of rotation of the couch/gantry coordinate system of the Linac by the use of a laser measuring device (laser displacement sensors), having fractions of a millimeter of accuracy, which device is attached to the Linac gantry and emits a laser beam which projects onto and reflects off the surfaces of a precision reference box (or other such reference fixture or surface) for the purpose of precisely measuring and centering isocenters within the couch/gantry coordinate system.

In another aspect, the present invention is a system for aligning a radiosurgery/stereotactic radiotherapy system. The system includes a linear accelerator, including a gantry and a collimator, a couch, and a stereotactic reference system mounted on the couch. The system further includes a laser measuring device mounted on the gantry, the laser measuring device having a laser generator element for generating a laser light beam and a laser displacement sensor. The system also includes a reference fixture, attached to the stereotactic reference system, having at least one reflective surface for reflecting the laser light beam to the laser displacement sensor.

In another aspect, the present invention is a method for aligning a stereotactic system. The system includes a linear accelerator having a gantry, a laser measuring device mounted on the gantry, a stereotactic reference system, a reference fixture affixed to the stereotactic reference system, the stereotactic reference system having a stereotactic coordinate system. The method comprises determining an origin of the stereotactic coordinate system relative to the said laser measuring device; measuring an isocenter of a target structure located within the stereotactic reference system; and adjusting the stereotactic reference system within the reference fixture so that the isocenter is positioned at the origin.

In yet another aspect, the present invention is an apparatus for aligning a stereotactic system, the stereotactic system including a linear accelerator having a gantry, a couch, and a stereotactic reference system mounted on the couch. The apparatus comprises generating means, mounted on for gantry, for generating a laser light beam; reflecting means, attached to the stereotactic reference system, for reflecting the laser light beam; and sensing means, mounted on the gantry, for measuring a distance between the reflecting means and the sensing means.

It is to be understood that both the foregoing general description and the following detailed description are exemplary and explanatory only and are not restrictive of the invention, as claimed.

The accompanying drawings are included to provide a further understanding of the invention and are incorporated in and constitute a part of this specification, to illustrate the embodiments of the invention, and, together with the description, to explain the principles of the invention.

BRIEF DESCRIPTION OF THE DRAWINGS

FIG. 2 shows a Linac with stereotactic collimators mounted on the gantry and stereotactic headring mounted on the couch.

FIG. 3 is an enlarged view of couch and gantry with laser measurer (laser displacement sensor) mounted on the gantry of the Linac to the left of the collimators.

FIG. 7 illustrates the determination (measurements) of a stereotactic target position (isocenter) at 5 cm inferior (posterior) and positioned within the Linac couch/gantry coordinate system.

FIG. 8 illustrates the determination (measurements) of a stereotactic target position (isocenter) at 5 cm anterior and positioned within the Linac couch/gantry coordinate system.

DETAILED DESCRIPTION OF THE INVENTION

Reference will now be made in detail to the present preferred embodiment of the invention, an example of which is illustrated in the accompanying drawings. Wherever possible, the same reference numbers will be used throughout the drawings to refer to the same or like parts.

In accordance with the present invention, a laser measuring apparatus and method are provided for aligning a Linac-based radiosurgery/stereotactic radiotherapy system. The laser measuring system for radiosurgery and radiotherapy alignment of the present invention comprises: hardware components that can be used by a neurosurgeon, radiation oncologist, radiation physicist, or technician familiar with the use of Linacs for the performance of radiosurgery/stereotactic radiotherapy; and means for accurately measuring and aligning the isocenter(s) of a treatment volume within a patient's body at the center or origin of axial rotation of the Linac couch/gantry system for the purpose of performing such radiosurgery or radiotherapy.

The invention is particularly useful for the practice of radiosurgery/stereotactic radiotherapy in which a couchmount-type stereotactic frame or reference system is used in the performance of such radiosurgery/stereotactic radiotherapy. The invention is also useful for reducing and/or eliminating errors in stereotactic positioning and localization due to couch or gantry sag, tilt, or rotation by directly measuring the isocenter's position relative to a fixed laser measuring source mounted on the Linac gantry. The method and apparatus of the invention is capable of measurements to within 1000th's of a millimeter.

In the preferred embodiment, the laser measuring system for radiosurgery/stereotactic radiotherapy alignment is initially calibrated by determining the zero reference point or origin of the stereotactic coordinate system (about which a precision localization box is attached) relative to a fixed laser displacement sensor mounted on the Linac gantry. The gantry and couch rotate about a common center that is the origin of the couch/gantry coordinate system. In the art of Linac-based stereotaxy, the stereotactic headring (or other such reference fixtures or surfaces) represents another coordinate system about the head or body part that is adjusted to be aligned within the couch/gantry coordinate system. Target point volumes within the reference coordinate system are, therefore, aligned to be coincident with the Linac coordinate system. The laser displacement sensor is capable of measuring distances in fractions of a millimeter. Such calibration measurements are used in subsequent positioning of a patient's body part, having the attached stereotactic reference system, within the origins of the Linac couch/ gantry system for the purpose of performing radiosurgery/ stereotactic radiotherapy.

Figure 1A:
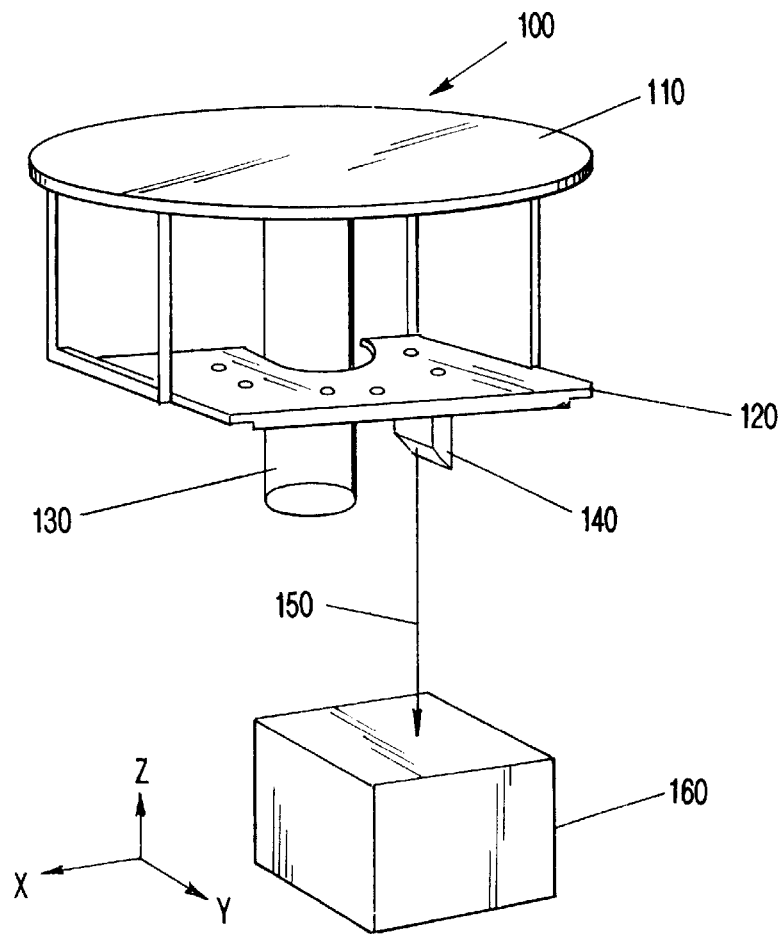
FIG. 1A illustrates the laser measuring assembly mounted on a Linac gantry.
Figure 1B:
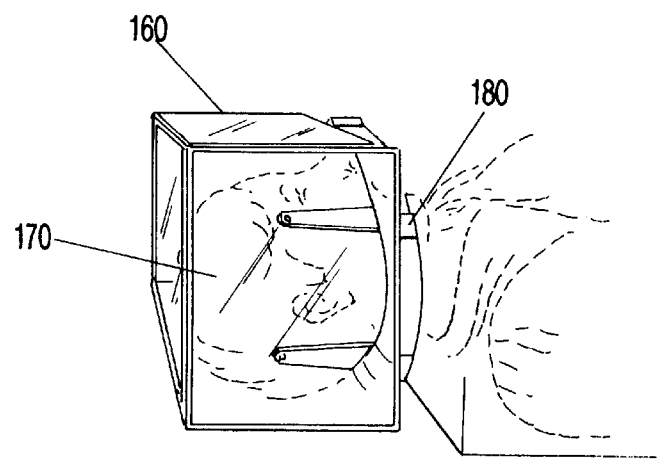
FIG. 1B illustrates the stereotactic headring with the stereotactic localization box fitted to a patient's head.

An exemplary embodiment of the laser measuring system for radiosurgery/stereotactic radiotherapy alignment of the present invention is shown in FIGS. 1A, 1B, and 3 and is designated generally by reference numerals 100 and 300. This embodiment can be practiced by practitioners knowledgeable in the art of radiotherapy for the purpose of reducing or eliminating errors due to misalignment of room laser alignment systems and errors due to couch/gantry sag, tilt, and rotation inherent in couchmount radiosurgery/ stereotactic radiotherapy systems. The apparatus allows consistent and accurate measurements of stereotactic coordinates and eliminates reliance on intersecting room laser lights for the purpose of aligning stereotactic coordinates.

An exemplary method of the invention is illustrated in FIGS. 5, 6, 7, and 8. Preferably, in this method, laser measurements are performed relative to a precision square or rectangular box placed around the stereotactic reference system to which the patient's head or body part is attached. Alternatively, non-rectangular reference structures or surfaces may be attached or fixed to a patient's body part (for the purpose of performing stereotactic localization of target volumes or isocenters within the patient's body), and the laser beams of the laser measuring device can be reflected off such surfaces at various fixed angular positions of the gantry about the patient's body for the purpose of measuring a given isocenter. One or more laser measuring devices (laser displacement sensors) can be employed in the practice of the invention. The preferred steps for practicing the method of the present invention comprise the major steps of:

A. Initial Calibration—Determining the Zero Reference or Origin of the Stereotactic Coordinate System. In this step, the zero reference point or origin of a stereotactic coordinate system (either frame-based or frameless) is determined relative to one or more fixed laser measuring devices (laser displacement sensors) mounted on the Linac gantry.

B. Adjusting by Laser Measurement the Stereotactic Coordinates of an Isocenter to the Linac Couch/Gantry Origin. In this step, the stereotactic coordinates of other stereotactic points within the stereotactic coordinate system are precisely measured by adjustments relative to the zero reference point or origin as determined by appropriately measured coordinate displacement values in relation to the fixed laser measuring device mounted on the Linac gantry.

Step A above may include the performance of various substeps, including, but not limited or solely confined to:

A1. Positioning on, or affixing to, the couch of the Linac system a stereotactic headframe with attached localization box (or appropriate attached reference fixtures or surfaces);

A2. Using a phantom test target to precisely align the stereotactic center (zero reference point or origin) of the localization box (or appropriate attached reference fixtures or surfaces) for the stereotactic headframe in the center of the couch/gantry coordinate system of the Linac in a manner known in the art. See W. L. Lutz, et al., A System for Stereotactic Radiosurgery with a Linear Accelerator, 14 Int'l J. Radiation Oncology and Biological Physics 373 (1988);

A3. Confirming the origin (zero position) by taking anterior/posterior and lateral x-rays with the Linac and incrementally adjusting the zero position or origin so that it is precisely aligned in the center of the couch/ gantry coordinate system in a manner known in the art. See Lutz, et al., supra;

A4. Attaching the laser measuring device (laser displacement sensor) to the gantry of the Linac in a fixed and relocatable position;

A5. Rotating the Linac gantry around the localization box in all three coordinate planes to measure the distance of the sides (surfaces) of the localization box from the laser measuring device when the laser beams of the measuring device are perpendicular to the sides (surfaces) of the localization box (or other such reference fixtures or surfaces). See FIG. 6. Measurements of the isocenter in relation to the top of the localization box would require positioning the couch along the axis of rotation of the gantry;

A6. Recording for future calculations the measured values of the distances of the sides (surfaces) of the localization box from the fixed laser displacement sensor, which position represents the spatial position of the localization box (or other such reference fixtures or surfaces) when it is positioned so that the origin of the stereotactic coordinate system (zero reference or origin) is coincident with the origin or center of the couch/gantry axis of rotation; and A7. Alternatively, when other reference fixtures or surfaces are used, laser measurements can be made to a non-orthogonal reference fixture or surface by placing the gantry at fixed angles along which the distance from the laser measurer to the reflected surfaces are measured. At least three such angles would be required for localization in this manner.

Step B above may include the performance of various substeps, including, but not limited or solely confined to:

B1. Affixing the stereotactic headframe or appropriate reference fixtures or surfaces to the patient's body part and determining the stereotactic coordinates of a target volume or structure by the use of computer tomographic scanning, MR scanning, angiographic imaging, isotope imaging, as in U.S. Pat. Nos. 5,099,846 and 5,398,684;

B2. Mounting the patient's body part with attached stereotactic reference system to the Linac couch (table);

B3. Using the laser measuring device to adjust the stereotactic frame with the localization box (or other such reference fixtures or surfaces) to the desired stereotactic isocenter coordinates so that such coordinate point (isocenter) is precisely positioned at the origin of the Linac couch/gantry coordinate system. This is achieved by adding and/or subtracting the displacement values relative to the previously measured distances (zero reference or origin) of the sides (surfaces) of the localization box to the fixed laser measuring device. See FIGS. 7 and 8. An alternative method, as noted above, can be used if non-orthogonal angles are employed in the localization.

Figure 4:
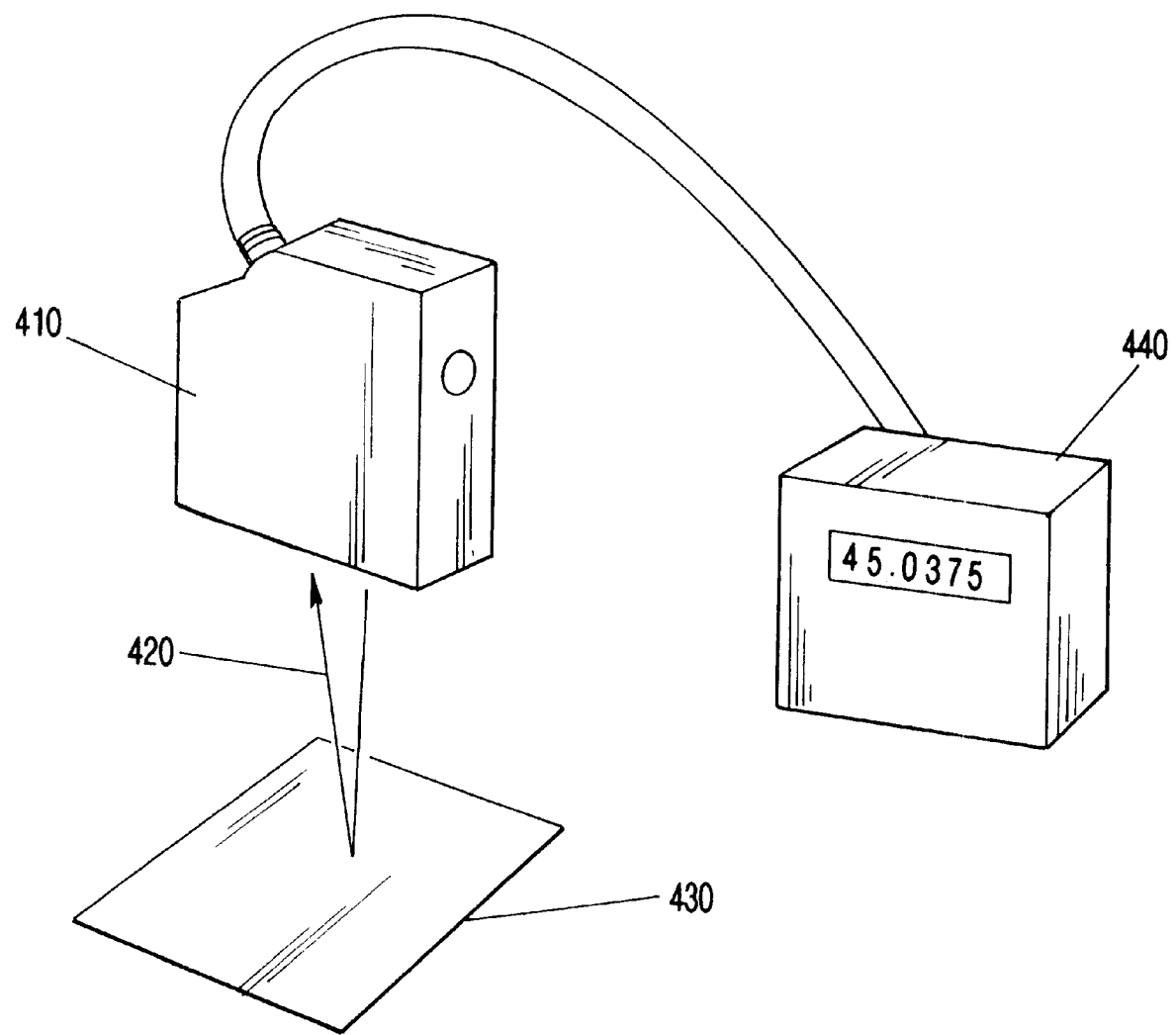
FIG. 4 is a diagrammatical representation of a laser displacement sensor with digital readout meter for distances measured to 1000ths of a millimeter.

FIG. 1A illustrates a preferred hardware diagram of the laser measuring assembly 100 mounted on the Linac gantry 110 to which a laser calibration plate 120 with attached laser measurer (laser displacement device) 140 is attached. The laser calibration plate is fitted about the collimator housing 130. The gantry 110 with the collimator housing 130, and the laser measurer 140 can be positioned in relation to a precision stereotactic localization box 160 (or other such reference fixtures or surfaces) that are attached to or positioned on the Linac couch. The laser measurer 140 (laser displacement device) emits a laser beam 150 which reflects off the surface of the laser localization box 160 and returns to the laser displacement sensor, as in FIG. 4, for precisely measuring, in fractions of a millimeter, the distance of the surface of the localization box 160 from the fixed position of the laser measurer 140.

Figure 5:
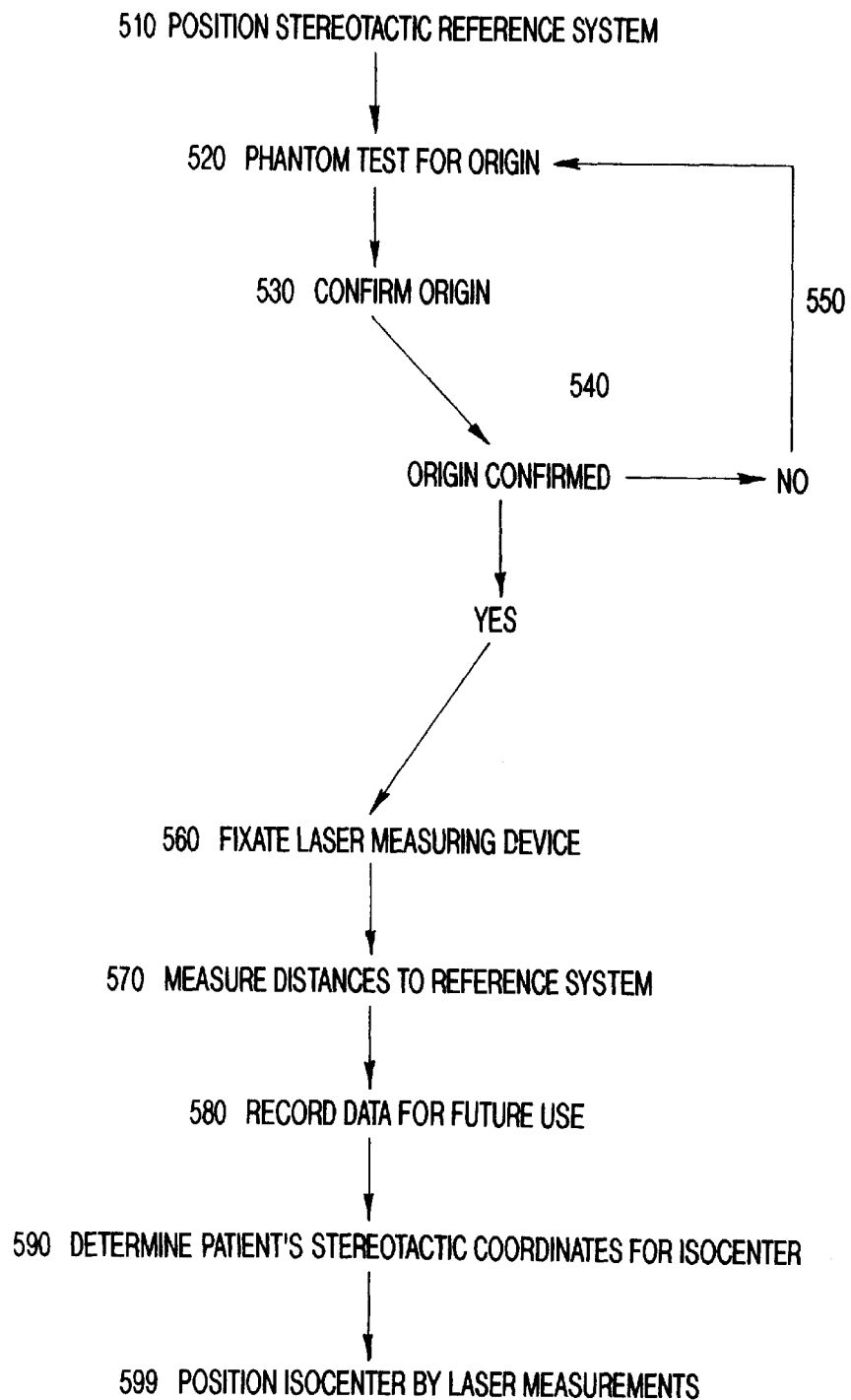
FIG. 5 is a flow chart of laser measuring system for radiosurgery or stereotactic radiotherapy alignment.

The laser measuring box 160, which is shown in FIG. 1B around a patient's head 170, may be used in conjunction with the stereotactic frame and a phantom device for initial calibration and set-up, as noted in the preferred steps for the practice of the method of the present invention, and illustrated in FIG. 5. The laser measuring box 160 may also be positioned about the patient's head (or body part) 170 for subsequent alignment of the stereotactic reference system within the Linac couch/gantry system, as also noted in the preferred steps for practicing the method of the invention and FIG. 5. The localization box 160 is a precision device preferably having square sides with smooth surfaces for performing accurate laser measurements, and the localization box 160 can be fitted around any stereotactic frame 180 (see FIG. 1B).

With reference to FIG. 2, reference numeral 200 depicts a conventional Linac configured for couchmount-type radiosurgery/stereotactic radiotherapy with a stereotactic collimator 130 mounted on the gantry 110 and a stereotactic headring 230 mounted on the couch 240. As noted above, the gantry 110 and couch 240 rotate about a common center (which is indicated in FIG. 2 by the intersection of Lines T and G) that is the origin of the couch/gantry coordinate system.

A preferred apparatus of the invention is illustrated in FIG. 3 (indicated by reference numeral 300). FIG. 3 shows the Linac couch 240 and gantry 110, depicted in FIG. 2, to which the laser measurer (laser displacement sensor) 140 is mounted on the gantry 110 adjacent to the collimator 130. The stereotactic headring 230 is fitted with the stereotactic localization box 160 and mounted to the end of the Linac couch 240. The laser measuring device 140 is positioned so that it is substantially perpendicular to a surface of the localization box 160 such that a laser beam can be reflected off that surface to measure the distance of that surface from the fixed position of the laser measurer 140. The measured distance is displayed on the digital readout (or other display means) (not shown) of the laser measurer 140, which digital readout may sit atop the couch surface.

The laser measurer (laser displacement sensor) 140 is commercially available and is a part of the preferred apparatus of the invention. The laser measurer 140 is further illustrated in FIG. 4, an exemplary measurer being described in the Keylance Laser Displacement Sensor LB1000 Series Instruction Manual, 1992. The laser measurer 140 may include a small housing 410 having a laser diode that emits a laser beam 420 capable of striking a given surface 430 at incremental distances from its fixed position, so that such laser beams 420 are reflected back to sensors contained within the housing 410. The laser sensors within the housing 410 can proportionately register the voltage output induced on a detector that is struck by the reflected laser beam, and such voltage output is proportional to the spatial distance of the reflected surface 430 from the laser measurer (laser displacement sensor) 140. The measured distance may be displayed in 1000th's of a millimeter on a digital readout meter 440.

FIG. 5 is a flow chart of the preferred method of the invention, and lists the steps employed in the practice of the invention. In the preferred method for use of the laser measuring system, a practitioner of the art of radiosurgery/stereotactic radiotherapy positions a given stereotactic reference system 510, with attached precision localization box 160, on a Linac couch 240, and performs phantom tests 520 to precisely align the zero reference, center, or origin of the stereotactic frame 230 in the center or origin of rotation of the Linac couch/gantry system. Confirmation x-rays 530 of the phantom test targets are incrementally taken 540, 555 after the method described in Lutz, et al., supra, until the origin of the stereotactic coordinate system and the origin of the Linac couch/gantry system are precisely aligned. The laser measuring device 160 is mounted in a fixed position 560 on the Linac gantry 110 and is used to measure 570 the distances of the sides (surfaces) of the localization box 160 from the laser measuring device 140 when the origins of the two coordinate systems, stereotactic reference system and couch/gantry system are aligned.

The gantry 110 is rotated about the localization box 160 and measurements may be taken from all surfaces, including the top of the localization box, requiring that the table (or couch) be rotated to a plane coincident with the gantry axis of rotation for such measurements. The measurement data is recorded (saved) 580 for future measurements and calibration. The stereotactic reference system is thereafter fixed to the patient's head or body part, and appropriate localization studies, such as computer tomographic scans, magnetic resonance scans, angiographic scans, isotope scans or x-rays, are used to stereotactically define a target volume and isocenter 590 within the patient's body in a manner disclosed in U.S. Pat. Nos. 5,099,846; 5,398,684; 5,205,289; and, 5,339,812. The displacement values of the determined isocenter(s) of the target volume in different dimensions is determined in relationship to the origin of the stereotactic reference system in a manner noted in FIGS. 6, 7, and 8. The determined isocenter(s) is positioned within the couch/gantry coordinate system by appropriate measurements 599 in each dimension to align the isocenter(s) at the couch/gantry origin.

Figure 6:
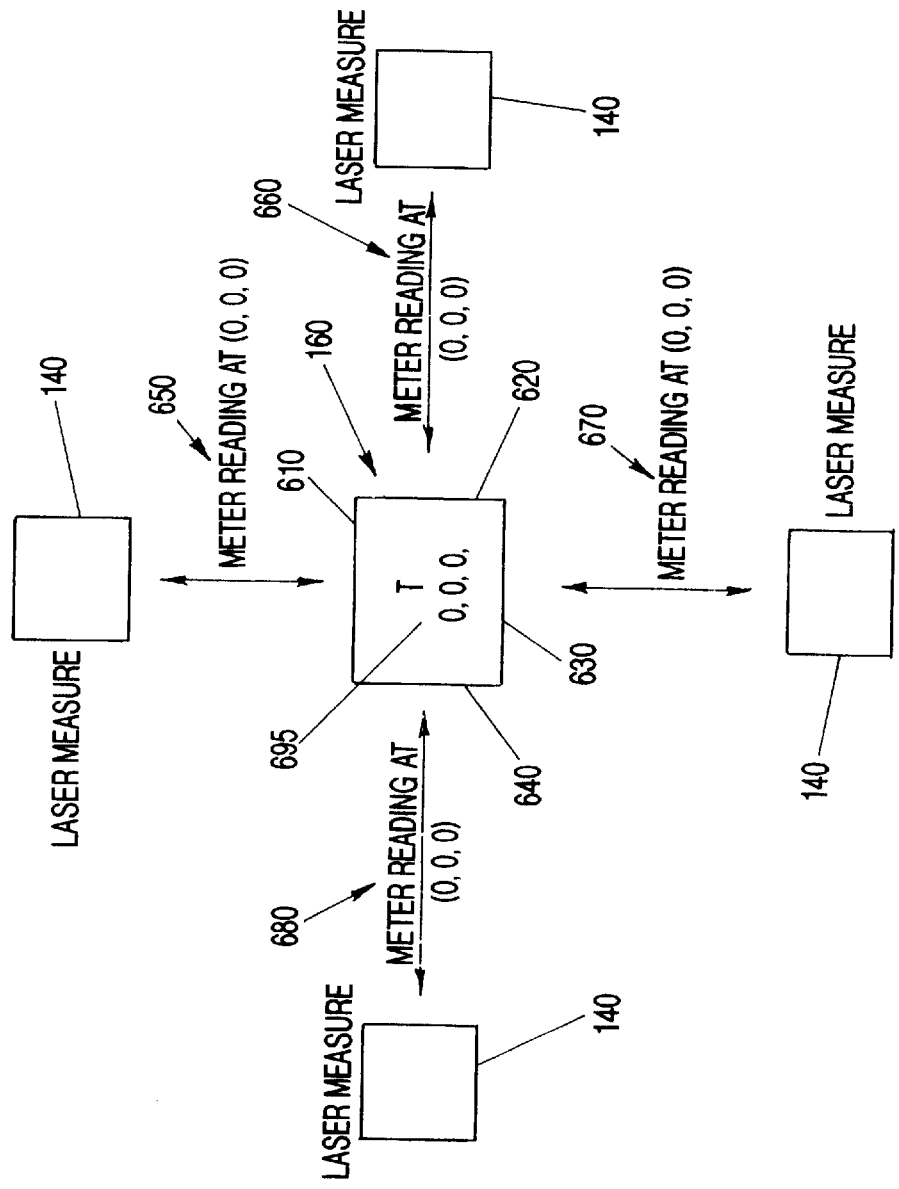
FIG. 6 is a diagrammatical representation of determination of zero reference or origin of stereotactic coordinate system within a Linac couch/gantry coordinate system.

FIG. 6 illustrates a use of the method and apparatus of the present invention of Step A above, i.e., "Initial Calibration— Determining the Zero Reference or Origin of the Stereotactic Coordinate System." In the practice and use of the apparatus, the precision localization box 160 may be attached to the stereotactic reference system, which is affixed to the Linac couch 240. The phantom test target 695 is positioned at the origin (for example, as shown at X=0, Y=0, Z=0) of a standard stereotactic frame reference system. X-ray localization and phantom test films are taken with the Linac to confirm that the phantom target "T" 695 at the center of the stereotactic reference system is positioned at the center of rotation of the couch/gantry coordinate system.

Still referring to FIG. 6, the precision localization box 160 has sides 610, 620, 630, 640 that may be square and may have smooth, flat surfaces that can reflect a laser light. As described above, the laser measuring device (laser displacement sensor) 140 is mounted in a fixed position on the Linac gantry 110, and the gantry with the laser measuring device 140 is rotated about the precision localization box 160, so that the measuring device 140 is perpendicular at various angles to the surfaces 610, 620, 630, 640 of the localization box 160. In each position, the meter readings 650, 660, 670, 680 are read to record for future calculations the distance of the sides 610, 620, 630, 640 of the localization box 160 from the laser measuring device 140 when the reference system is calibrated at the origin of the stereotactic coordinate system. FIG. 6 is a diagram of such measurements along the "X" and the "Z" ordinates (also see FIG. 1). In order to obtain a calibration measurement for the "Y" coordinate, (see FIG. 1), the couch 240 is rotated so that it is in the plane of rotation of the gantry 110, and the gantry is aligned so that it is perpendicular to the localization box 160 along the horizontal plane. This would not be required in an embodiment in which multiple laser measuring devices (laser displacement sensors) are attached to various other sites on the gantry.

FIGS. 7 and 8 are diagrams of the use of the method and apparatus of the patent of Step B, "Adjusting by Laser Measurements the Stereotactic Coordinates of an Isocenter to the Linac Couch/Gantry Origin." In the practice and use of the apparatus for the localization measurement of a given target position, the distances (displacement values) of a new target 710, 810 are added or subtracted to the calibration value at a given position of the Linac gantry 110 to the precision localization box 160 in order to determine the new laser measurement for positioning of that target (isocenter) 710, 810 at the center of rotation of the Linac couch/gantry system.

For example, FIG. 7 demonstrates a target position 710 at 5 cm inferior (posterior along the "Z" ordinate). In this example, in order to position the Linac couch/gantry center of rotation at this new target 710, the stereotactic reference box 160 would have to be shifted 5 cm anteriorally. Thus, the meter reading when the gantry is perpendicular to the anterior surface 720 would be the meter reading at zero minus 5 cm 730, and a meter reading of the zero meter reading plus 5 cm 740 when the gantry is positioned perpendicular to the posterior surface of the localization box 160. For this new target, there would be no change in the meter readings from the zero reference 750, 760 when the Linac gantry is positioned perpendicular to either the left 770 or the right 780 side of the localization box 160.

Referring now to FIG. 8, likewise, the same method is practiced when the target 810 is positioned at 5 cm anterior. In this example, in order to position the Linac couch/gantry center of rotation of this new target 810, the stereotactic reference box 160 would have to be shifted 5 cm posteriorally. Thus, the meter reading when the gantry is perpendicular to the anterior surface 820 would be the meter reading at zero plus 5 cm 830, and a meter reading of the zero meter reading minus 5 cm 840 when the gantry is positioned perpendicular to the posterior surface 850 of the localization box 160. For this new target, there would be no change in the meter readings from the zero reference 860, 870 when the Linac gantry is positioned perpendicular to either the left 880 or the right 890 side of the localization box 160. In both examples, FIGS. 7 and 8, the meter readings would be the same as the zero meter readings when measurements are taken along the "Y" ordinate (see FIG. 1).

FIGS. 7 and 8 serve as examples of how laser measurements can be used to precisely locate new stereotactic reference targets (isocenters) within the Linac couch/gantry system. In another embodiment, a similar method can be used with other reference fixtures or surfaces having non-orthogonal surfaces. Additional embodiments can also use multiple laser displacement sensors to measure distances.

It will be apparent to those skilled in the art that various modifications and variations can be made in the apparatus and method of the present invention without departing from the spirit or scope of the invention. Thus, it is intended that the present invention cover the modifications and variations of this invention, provided they come within the scope of the appended claims and their equivalents.

What is claimed is:

1. A method for aligning the isocenter(s) of a target treatment volume in a linear accelerator based radiosurgery/stereotactic radiotherapy system, the system having a couch and gantry, a stereotactic couch/gantry coordinate system with a couch/gantry axis of rotation, and at least one laser measuring device, comprising the steps of:

determining a zero reference point of a stereotactic coordinate system within the couch/gantry coordinate system relative to the laser measuring device; and adjusting by laser measurement the stereotactic coordinates of the isocenter(s) of the target treatment volume to the center of the couch/gantry coordinate system.

2. The method of claim 1 wherein the step of determining a zero reference point comprises aligning the zero reference point of the stereotactic coordinate system with the center of the couch/gantry coordinate system.

3. The method of claim 2 wherein the step of aligning the zero reference point comprises:

using a phantom test target at the zero reference point;

taking images of the phantom target with the radiotherapy system; and incrementally adjusting the zero reference point so that it is aligned with the center of the couch/gantry coordinate system.

4. The method of claim 1 wherein the step of adjusting by laser measurement comprises:

determining the stereotactic coordinates of the target treatment volume relative to the zero reference point of the stereotactic coordinate system;

placing the target treatment volume upon the couch; and adjusting the zero reference point of the stereotactic coordinate system to position the target treatment volume at the center of the couch/gantry coordinate system.

5. The method of claim 4 wherein the step of adjusting the zero reference point comprises shifting the position of the reference fixture relative to the at least one laser measuring device.

6. The method of claim 4 wherein wherein the target treatment volume is within a patient's body, and the step of placing the target treatment volume comprises:

attaching a reference fixture about a body part of the patient;

mounting the patient's body part to the couch; and performing laser measurements relative to the reference fixture attached about the body part to obtain stereotactic localization of isocenter(s) of the target treatment volume within the patient's body.

7. The method of claim 1 wherein the at least one laser measuring device comprises more than one laser measuring devices.

8. The method of claim 1, wherein the laser measuring device comprises a laser displacement sensor, and the step of determining the zero reference point comprises:

providing a reference fixture about the target treatment volume to be aligned;

removably attaching the at least one laser displacement sensor to the gantry;

rotating the gantry around the reference fixture; and performing first laser measurements of at least three different distances between the at least one laser displacement sensor and the reference fixture.

9. The method of claim 8 wherein the step of performing first laser measurements comprises reflecting a laser beam from the at least one laser measuring device off the reference fixture at a plurality of angular positions of the gantry relative to the reference fixture.

10. The method of claim 8 wherein the step of determining a zero reference point further comprises recording for future calculations the first measured values of the three distances between the laser displacement sensor and the reference fixture.

11. The method of claim 10 wherein the step of recording for future calculations the first measured values of the three distances between laser displacement sensor and the reference fixture comprises the step of obtaining thereby a position of the reference fixture representing the spatial position of the reference fixture when the zero reference point of the stereotactic coordinate system is coincident with the center of the couch/gantry coordinate system.

12. The method of claim 8 wherein the step of adjusting by laser measurement comprises:

determining the stereotactic coordinates of the target treatment volume relative to the zero reference point of the stereotactic coordinate system;

placing the target treatment volume upon the couch; and adjusting the reference fixture to position the target treatment volume at the center of the couch/gantry coordinate system.

13. The method of claim 12 wherein the step of adjusting the reference fixture comprises:

performing second laser measurements of at least three different distances between the at least one laser displacement sensor and the reference fixture;

determining at least one displacement value from the first laser measurements and the second laser measurements; and shifting the reference fixture relative to the at least one laser displacement sensor.

14. The method according to claim 13 wherein the step of shifting the reference fixture further comprises shifting the reference fixture a distance approximately equal to the at least one displacement value.

15. The method of claim 13 wherein the step of shifting the reference fixture further comprises steps selected from the group consisting of:

adding displacement values, relative to the obtained zero reference point of the couch/gantry coordinate system, to the second laser measured distances from the surface of the reference structure to the laser measuring device; and subtracting displacement values, relative to the obtained zero reference point of the couch/gantry coordinate system, from the second laser measured distances from the surface of the reference structure to the laser measuring device.

16. The method of claim 13 wherein the at least one laser measuring device generates a laser beam and wherein the step of performing second laser measurements comprises:

rotating the gantry around the reference fixture; and measuring the distance between the reference fixture and the laser measuring device.

17. The method of claim 16 wherein rotating the gantry further comprises:

positioning the gantry at least three fixed angles to the reference fixture; and measuring the distance between the laser measuring device and the reference fixture along the at least three angles.

18. The method of claim 13 wherein the step of shifting the reference fixture further comprises steps selected from the group consisting of:

adding displacement values, relative to the obtained zero reference point of the couch/gantry coordinate system, to the second laser measured distances from the surface of the reference structure to the laser measuring device; and subtracting displacement values, relative to the obtained zero reference point of the couch/gantry coordinate system, from the second laser measured distances from the surface of the reference structure to the laser measuring device.

19. An apparatus for aligning the isocenter of a target treatment volume for a linear accelerator based radiosurgery/stereotactic radiotherapy system, the system having a couch, a gantry, and a couch/gantry coordinate system, comprising:

means for laser measuring distances from the couch/gantry coordinate system to the target volume; and means for using the laser measured distances to align the isocenter(s) of the target volume within the center of rotation of the couch/gantry coordinate system.

20. A system for aligning a stereotactic target volume having isocenters within a coordinate system having centers of rotation, comprising:

a linear accelerator having a gantry and a collimator;

a couch;

a stereotactic reference fixture having at least one reflective surface for receiving and for reflecting a laser light beam; and a laser measuring device mounted on said gantry, said laser measuring device comprising a laser generating means for generating the laser light beam and sensing means for receiving the reflected laser light beam from said reference fixture and for measuring a distance between said reflective surface of said reference structure and said sensing means.

21. A system according to claim 19 wherein said reference fixture comprises at least two orthogonal reflective surfaces.

22. A system according to claim 19 wherein said reference fixture comprises at least two non-orthogonal surfaces.

* * * * *